United States Patent [19]

Sakamoto et al.

[11] Patent Number: 4,919,113
[45] Date of Patent: Apr. 24, 1990

[54] METHOD OF CLEANING SCOPE END OF ENDOSCOPE AND ENDOSCOPE WITH SCOPE END CLEANING MECHANISM

[75] Inventors: Yutaka Sakamoto, Fukushima; Ryuichi Kamaga, Tochigi, both of Japan

[73] Assignee: Kabushiki Kaisha Toshiba, Kawasaki, Japan

[21] Appl. No.: 361,976

[22] Filed: Jun. 6, 1989

[30] Foreign Application Priority Data

Jun. 10, 1988 [JP] Japan .................. 63-141692

[51] Int. Cl.$^5$ ............................. A61B 1/12
[52] U.S. Cl. ...................................... 128/4
[58] Field of Search ..................... 128/4, 4 A

[56] References Cited

U.S. PATENT DOCUMENTS 4,402,310 9/1983 Kimura .................. 128/4 A
4,509,507 4/1985 Yabe ...................... 128/4 A
4,844,052 7/1989 Iwakoshi ................... 128/4

Primary Examiner—William H. Grieb
Attorney, Agent, or Firm—Foley & Lardner, Schwartz, Jeffery, Schwaab, Mack, Blumenthal & Evans

[57] ABSTRACT

A method of cleaning scope end of endoscope capable of performing a painless cleaning operation as well as securing a stable direct observation condition, without relying on an operator's skill. The method includes the steps of: injecting water towards the scope end for washing out the scope end; exhaling air towards the scope end to blow away remaining drops on the scope end of the water injected at the injecting step; and inhaling as much an amount of air as exhaled at the exhaling step, slowly enough not to cause dew condensation due to an abrupt pressure decrease. An endoscope equipped with scope end cleaning mechanism performing this method is also disclosed.

14 Claims, 6 Drawing Sheets

METHOD OF CLEANING SCOPE END OF ENDOSCOPE AND ENDOSCOPE WITH SCOPE END CLEANING MECHANISM

BACKGROUND OF THE INVENTION

1. Field of the Invention

The present invention relates to an endoscope equipped with a mechanism for cleaning a scope end where exposed ends of optical devices such as object lens and light guide are located and, more particularly, to such a scope end cleaning mechanism in which water injections, air inhalation and air exhalation are utilized.

2. Description of the Background Art

A conventional endoscope, either of fiber scope type or of electronic endoscope type, is usually equipped with a mechanism for cleaning contamination due to gastric juice of a scope end where exposed ends of optical devices such as object lens and light guide are located, which normally comprises a water injection to wash out the gastric juice on the scope end and an air exhalation or blowing to blow away remaining water drops from the scope end.

Such a cleaning often includes additional air inhalation for the purpose of reducing a gastric inner pressure increased by the water injection and the air exhalation, as an increased gastric inner pressure is known to cause some pain for a patient at a level which varies for different patients.

A sequential operation of such water injection, air exhalation and air inhalation has conventionally been carries out by an operator who controls separate switches provided for activating each of these functions. Thus, a painless cleaning operation depended very much on the operator's skill.

The skill of the operator becomes also essential in such a conventional endoscope in a view that an abrupt dropping of 8 to 15 Torr in the gastric inner pressure by the air inhalation can produce dew condensation due to a dropping of dew point, which will obstruct a satisfactory observation by befogging the optical devices at the scope end.

Furthermore, as it has become a fairly common practice in an endoscope to make various adjustments and modifications on directly observed images, securing of a stable condition for direct observations becomes a matter of great concern, but this can also be affected by the operator's skill in a conventional endoscope because of the problem of dew condensation just mentioned.

SUMMARY OF THE INVENTION

It is therefore an object of the present invention to provide a method of cleaning scope end of endoscope and an endoscope with scope end cleaning mechanism, capable of performing a painless cleaning operation as well as securing a stable direct observation condition, without relying on an operator's skill.

According to one aspect of the present invention there is provided a method of cleaning a scope end of an endoscope, comprising the steps of: injecting water towards the scope end for washing out the scope end; exhaling air towards the scope end to blow away remaining drops on the scope end of the water injected at the injecting step; and inhaling substantially as much an amount of air as exhaled at the exhaling step, slowly enough not to cause dew condensation due to an abrupt pressure decrease.

According to another aspect of the present invention there is provided an endoscope with scope end cleaning mechanism which utilizes water injections, air inhalation and air exhalation, comprising: a scope with a scope end where exposed ends of optical devices are located; means for injecting water towards the scope end for washing out the scope end; means for exhaling air towards the scope end to blow away remaining drops on the scope end of the water injected by the injecting means; and means for inhaling substantially as much an amount of air as exhaled by the exhaling means, slowing enough not to cause dew condensation due to an abrupt pressure decrease.

Other features and advantages of the present invention will become apparent from the following description taken in conjunction with the accompanying drawings.

BRIEF DESCRIPTION OF THE DRAWINGS

FIG. 7 is a flow chart for a fifth embodiment of the scope end cleaning operation by the endoscope of FIG. 1.

DETAILED DESCRIPTION OF THE PREFERRED EMBODIMENTS

Figure 1:
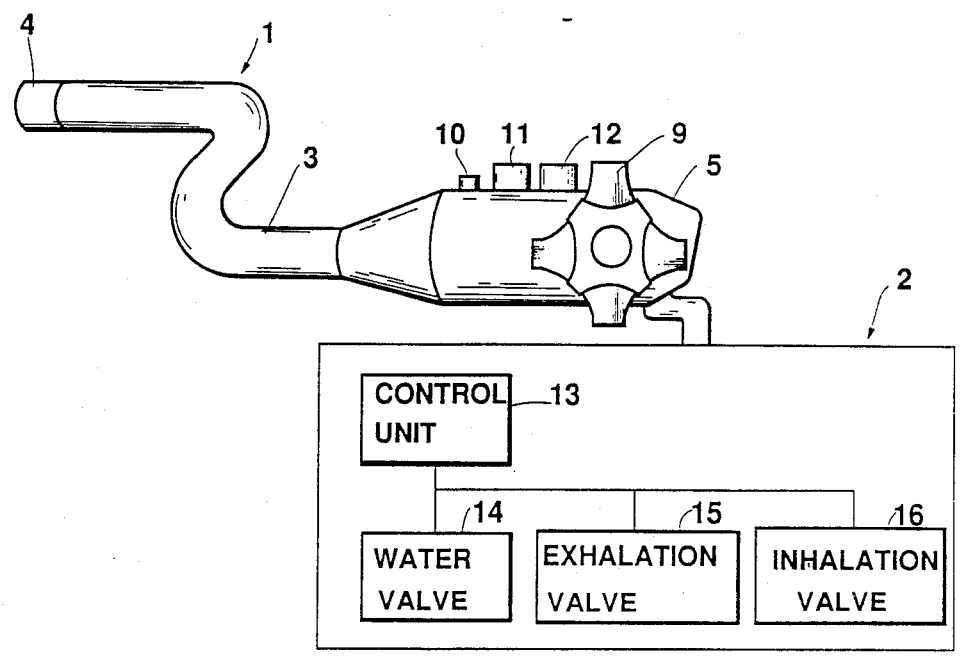
FIG. 1 is a schematic diagram of an endoscope according to the present invention.

Referring now to FIG. 1, there is shown one embodiment of a endoscope according to the present invention.

This endoscope comprises a scope 1 and a system body 2.

The scope 1 further comprises a flexible scope tube 3 having a solid scope end portion 4, and a operation handle 5 having an angle knob 9 for moving the solid end portion 4 in vertical and horizontal directions, an automatic cleaning switch 10 for activating an automatic cleaning operation sequence to be explained below, and an air exhalation switch 11 and a water injection switch 12 of conventional type which enable an operator to perform conventional air exhalation and water injection by manual operation.

Figure 2:
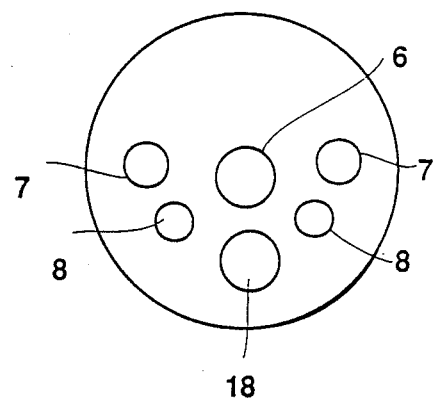
FIG. 2 is a plan view of a scope end of the endoscope of FIG. 1.

As shown in FIG. 2, a top of the scope end portion 4 has exposed ends of an object lens 6 and light guides 7, as well as apertures 18 for insertion of forceps and apertures 8 for water injection, air exhalation, and air inhalation.

The system body 2 includes a control unit 13 for controlling operations of an electromagnetic water valve 14, an electromagnetic exhalation valve 15, and an electromagnetic inhalation valve 16, each of which is connected to a water pump, an exhalation pump, and an inhalation pump, respectively, all of which are not shown in FIG. 1.

The controlling by the control unit 13 is determined by the manual operation by the operator of the automatic cleaning switch 10, the air exhalation switch 11 and the water injection switch 12. When the operator chooses manual operation of the air exhalation switch 11 and the water injection switch 12, the operation of this endoscope is substantially the same as that of a convention one, so that the explanation for this case will be omitted.

Figure 3:
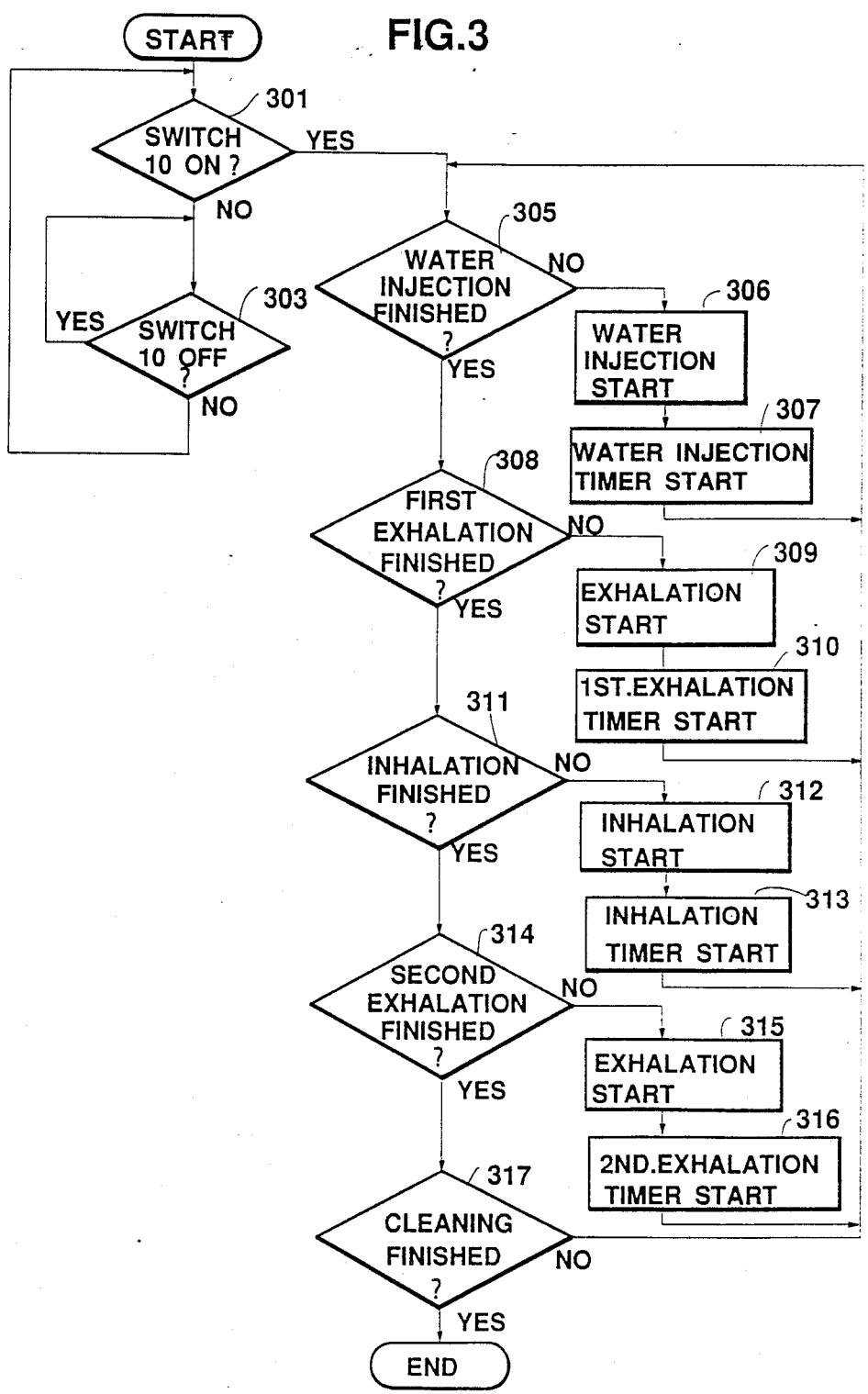
FIG. 3 is a flow chart for a first embodiment of a scope end cleaning operation by the endoscope of FIG. 1.

On the other hand, when the operator chooses the automatic cleaning by turning on the automatic cleaning switch 10, the following automatic cleaning operation sequence, shown in the flow chart of FIG. 3, will automatically be carried out under the control of the control unit 13.

First, at the steps 301 and 303, whether the automatic cleaning switch 10 is turned on or not is determined.

When the automatic cleaning switch 10 is turned on, the automatic cleaning is carried out in the following sequence.

At the step 305, whether the water injection is finished or not is determined. If so, the process proceeds to the step 308. Otherwise, at th step 36 the water injection is started out by opening the water valve 14, and at the step 307, a water injection timer which has been prepared to measure a predetermined time sufficient for washing out the scope end portion 4, is started to run. The water injection continues until the water injection timer stops at which time the water valve 14 is automatically shut. The process then returns to the step 305.

At the step 308, whether the first exhalation is finished or not is determined. If so, the process proceeds to the step 311. Otherwise, at the step 309 the exhalation is started out by opening the exhalation valve 15, and at the step 310, a first exhalation timer which has been prepared to measure a predetermined time sufficient for blowing away remaining water drops from the scope end portion 4, which may be different from that given for the water injection timer, is started to run. The first exhalation continues until the first exhalation timer stops at which time the exhalation valve 15 is automatically shut. The process then returns to the step 305.

At the step 311, whether the inhalation is finished or not is determined. If so, the process proceeds to the step 314. Otherwise, at the step 312 the exhalation is started out by opening the inhalation valve 16, and at the step 313, an inhalation timer which has been prepared to measure a predetermined time which gives an amount of inhalation in this step to be greater than an amount of preceding exhalation at the first exhalation, is started to run. The inhalation continues until the inhalation timer stops at which time the inhalation valve 16 is automatically shut. The process then returns to the step 305.

At the step 314, whether the second exhalation is finished or not is determined. If so, the process proceeds to the step 317. Otherwise at the step 315 the exhalation is started out by opening the exhalation valve 15, and at the step 316, a second exhalation timer which has been prepared to measure a predetermined time which gives a total amount of exhalation at the previous first exhalation and this second exhalation to be equal to the amount of inhalation at the preceding inhalation, is started to run. The second exhalation continues until the second exhalation timer stops at which time the exhalation valve 15 is automatically shut. The process then returs to the step 305.

Finally, at the step 317, whether all the operation of the cleaning is finished is determined. If so, the process returns to the step 305, otherwise the process terminates.

In this automatic cleaning operation sequence, the first exhalation, inhalation, and second exhalation are arranged in such an order that neither an excessive exhalation causing a painful inflation of gastric inner pressure nor an excessive inhalation causing dew condensation can occur.

Thus, it is possible in this endoscope to be capable of performing a painless cleaning operation as well as securing a stable direct observation condition, without relying on an operator's skill.

There are several variations of the automatic cleaning operation sequence of FIG. 3, which will now be explained with reference to FIGS. 4 to 7.

Figure 4:
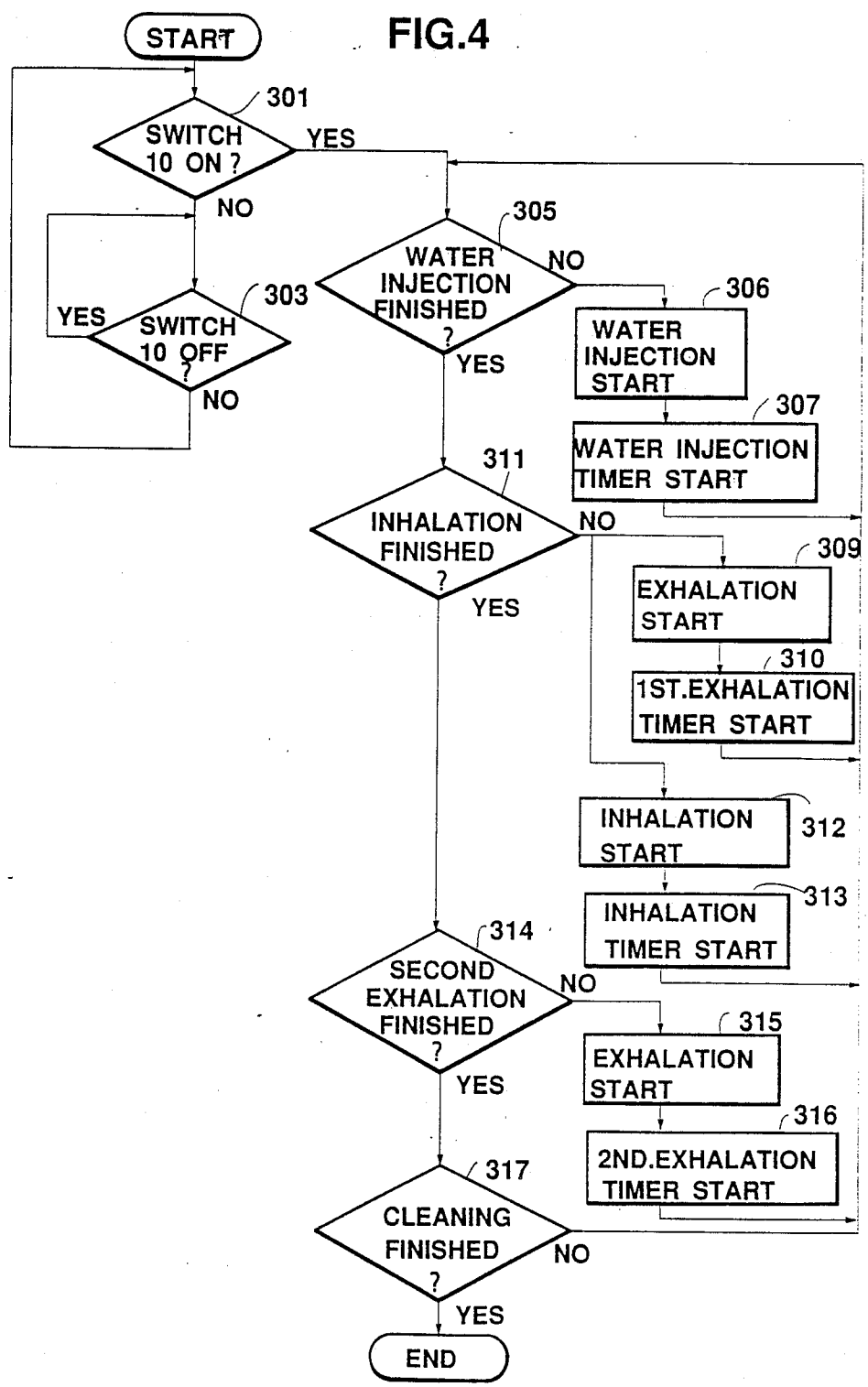
FIG. 4 is a flow chart for a second embodiment of the scope end cleaning operation by the endoscope of FIG. 1.

First, as shown in FIG. 4, the first exhalation at the step 309 and the inhalation at the step 312 may be carried out simultaneously in parallel.

Figure 5:
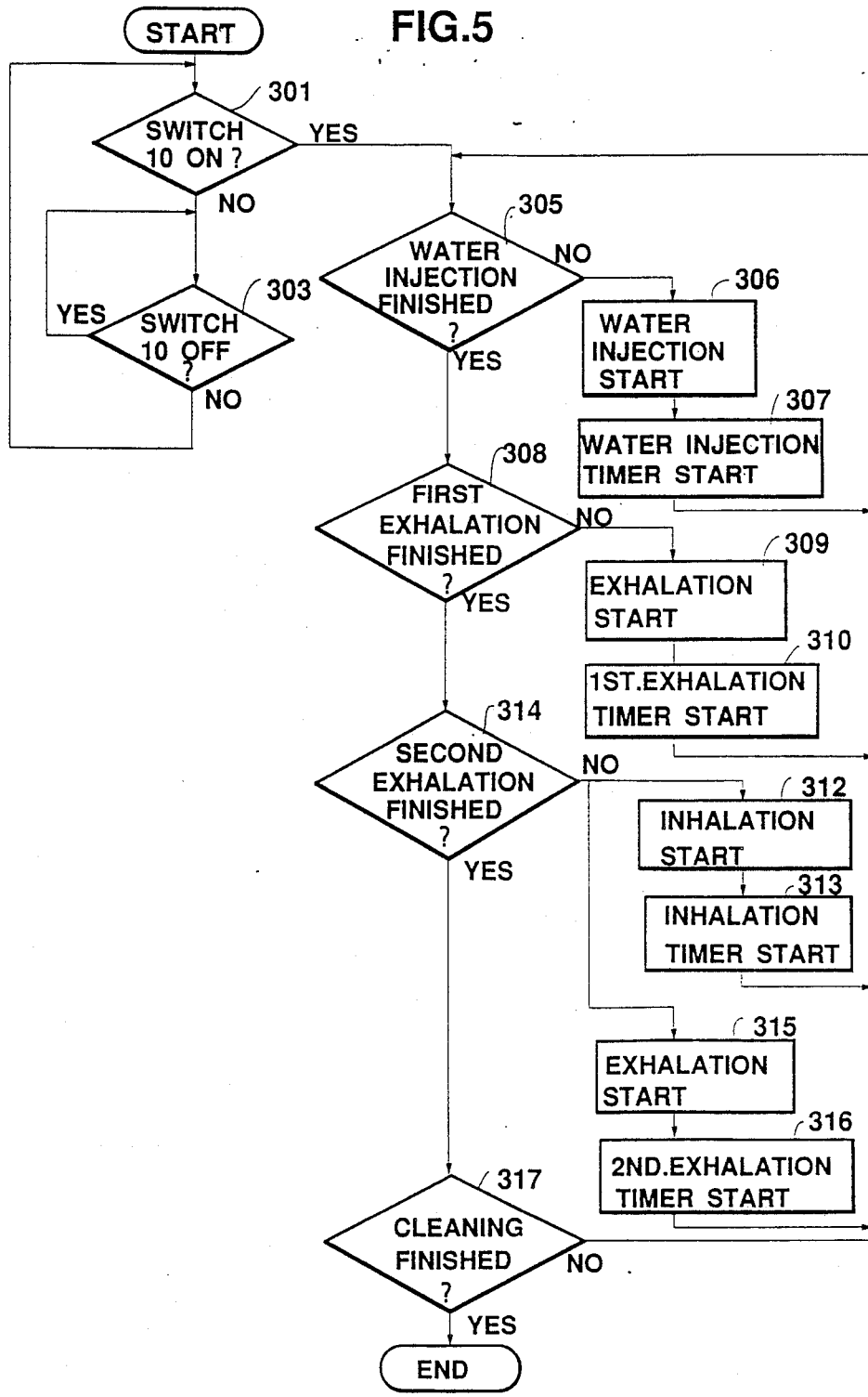
FIG. 5 is a flow chart for a third embodiment of the scope end cleaning operation by the endoscope of FIG. 1.

Alternatively, as shown in FIG. 5, the inhalation at the step 312 and the second exhalation at the step 315 may be carried out simultaneously in parallel.

Figure 6:
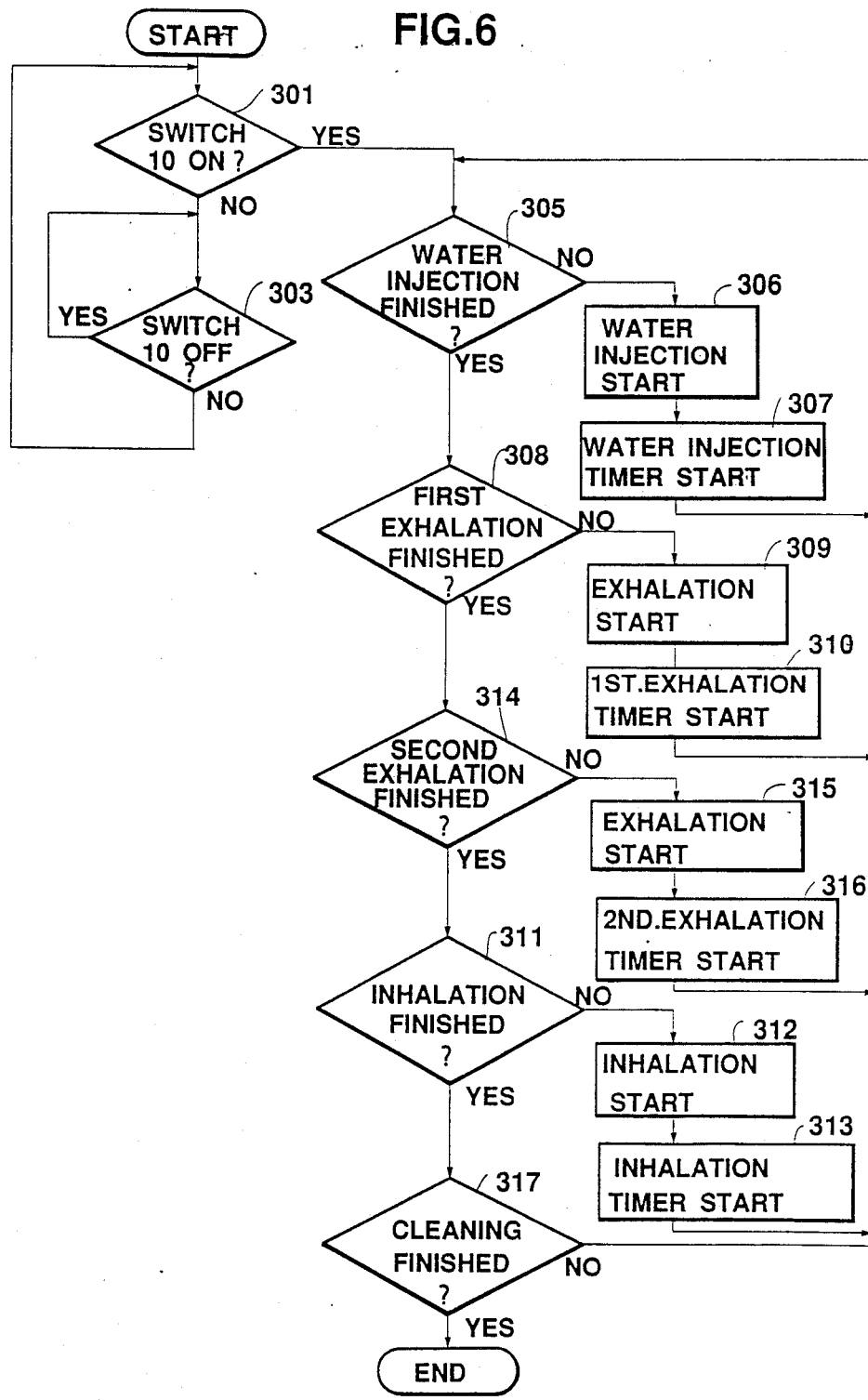
FIG. 6 is a flow chart for a fourth embodiment of the scope end cleaning operation by the endoscope of FIG. 1.

Also, as shown in FIG. 6, the order of the inhalation at the step 311 and the second exhalation at the step 315 may be switched when the amount to be exhaled and inhaled is relatively small. Here, obviously the the first exhalation and the second exhalation may be replaced by a single continuous exhalation.

Finally, as shown in Fig. The inhalation at the step 312 may be combined with a single exhalation at the step 315 to be carried out simultaneously in parallel. Here, at the step 318, whether the exhalation is finished or not is determined. If so, the process proceeds to the step 317. Otherwise, at the step 315 the exhalation is started out by opening the exhalation valve 15, and at the step 319, an exhalation timer which has been prepared to measure a predetermined time which gives an amount of exhalation to be equal to the amount of inhalation at the simultaneous inhalation, is started to run. The exhalation continues until the exhalation timer stops at which time the exhalation valve 15 is automatically shut. The process then returns to the step 305.

In all of these automtaic cleaning operation sequences, just as in the first one of FIG. 3, the exhalation and inhalation can be arranged in such an order that neither an excessive exhalation causing a painful inflation of gastric inner pressure nor an excessive inhalation causing dew condensation can occur.

It is obviously possible in the above variations to use a single common timer for two steps to be carried out simultaneously in parallel, in which case the amount of inhalation or exhalation at any given step can still be controllable by controlling flow rate through corresponding valves.

It is also to be noted that the automatic cleaning just described may be combined with an automatic means for detecting contamination of the scope end, to provide a totally automatic cleaning mechanism.

Besides these, many modifications and variations of the above embodiment may be made without departing from the novel and advantageous features of the present invention. Accordingly, all such modifications and variations are intended to be included within the scope of the appended claims.

What is claimed is:

1. A method of cleaning a scope end of an endoscope, comprising the steps of:
    injecting water on the scope end for washing out the scope end;

exhaling air on the scope end to blow away remaining drops on the scope end of the water injected at the injecting step; and inhaling substantially as much an amount of air as exhaled at the exhaling step, slowly enough not to cause dew condensation due to an abrupt pressure decrease.

2. The method of claim 1, wherein the exhaling step is divided into a first exhaling step preceding the inhaling step and a second exhaling step following the inhaling step.

3. The method of claim 1, wherein the exhaling step and the inhaling step are carried out simultaneously in parallel.

4. The method of claim 2, wherein the first exhaling step and the inhaling step are carried out simultaneously in parallel.

5. The method of claim 2, wherein the second exhaling step and the inhaling step are carried out simultaneously in parallel.

6. The method of claim 1, wherein a sequence comprising the injecting step, exhaling step and the inhaling step is carried out automatically.

7. The method of claim 6, wherein the sequence is initiated by an operator's manual operation of a switch which activates a contrrol unit controlling the sequntial performance of the injecting step, exhaling step and the inhaling step.

8. An endoscope with scope and cleaning mechanism which utilizes water injections, air inhalation and air exhalation, comprising:

a scope with a scope end where exposed ends of optical devices are located;

means for injecting water on the scope end for washing out the scope end;

means for exhaling air on the scope end to blow away remaining drops on the scope end of the water injected by the injecting means; and means for inhaling substantially as much an amount of air as exhaled by the exhaling means, slowly enough not to cause dew condensation due to an abrupt pressure decrease.

9. The endoscope of claim 8, wherein exhalation by the exhaling means is divided into a first exhalation preceding the inhalation by the inhaling means and a second exhalation following the inhalation by the inhaling means.

10. The endoscope of claim 8, wherein the exhalation by the exhaling means and the inhalation by the inhaling means are carried out simultaneously in parallel.

11. The endoscope of claim 9, wherein the first exhalation and the inhalation are carried out simultaneously in parallel.

12. The endoscope of claim 9, wherein the second exhalation and the inhalation are carried out simultaneously in parallel.

13. The endoscope of claim 8, wherein a sequence comprising the injection by the injecting means, exhalation and inhalation is carried out automatically.

14. The endoscope of claim 13, wherein the endoscope further comprises an automatic cleaning switch and a control unit, and wherein the sequence is initiated by an operator's manual operation of the automatic cleaning switch which activates the control unit controlling the sequential performance of the injection, exhalation and inhalation.

* * * * *